US010518918B2

(12) United States Patent
Lucani et al.

(10) Patent No.: US 10,518,918 B2
(45) Date of Patent: Dec. 31, 2019

(54) APPARATUS AND METHOD FOR STERILIZING RECEPTACLE CLOSURES

(71) Applicant: SIDEL PARTICIPATIONS S.A.S., Octeville-sur-Mer (FR)

(72) Inventors: Enrico Lucani, Parma (IT); Rossana Borgese, Parma (IT); Alessandro Mameli, Parma (IT); Fabrice Euzen, Parma (IT)

(73) Assignee: SIDEL PARTICIPATIONS, Octeville-sur-mer (FR)

( * ) Notice: Subject to any disclaimer, the term of this patent is extended or adjusted under 35 U.S.C. 154(b) by 295 days.

(21) Appl. No.: 15/405,699

(22) Filed: Jan. 13, 2017

(65) Prior Publication Data

US 2017/0203869 A1    Jul. 20, 2017

(30) Foreign Application Priority Data

Jan. 15, 2016   (EP) .................... 16305037

(51) Int. Cl.
*B65B 55/10* (2006.01)
*B65B 55/12* (2006.01)
(Continued)

(52) U.S. Cl.
CPC ............... *B65B 55/10* (2013.01); *A61L 2/20* (2013.01); *A61L 2/206* (2013.01); *A61L 2/22* (2013.01);
(Continued)

(58) Field of Classification Search
CPC . B65B 55/10; B65B 55/12; A61L 2/22; A61L 2/20; A61L 2/208
See application file for complete search history.

(56) References Cited

U.S. PATENT DOCUMENTS

| | | | |
|---|---|---|---|
| 2007/0157552 A1* | 7/2007 | Cirio ................. | B65G 47/5104 53/306 |
| 2011/0142731 A1* | 6/2011 | Beckmann .............. | A61L 2/208 422/292 |
| 2012/0183451 A1* | 7/2012 | Shi ......................... | B67B 3/003 422/302 |

FOREIGN PATENT DOCUMENTS

| | | |
|---|---|---|
| EP | 2546155 A1 | 1/2013 |
| EP | 2610209 A1 | 7/2013 |

(Continued)

OTHER PUBLICATIONS

European Search Report issued by the European Patent Office in counterpart European Patent Application No. 16305037.0, dated Jul. 12, 2016.

*Primary Examiner* — Kevin Joyner (57) ABSTRACT

A sterilization apparatus for sterilizing receptacle closures, comprising: a treatment chamber having an inlet station and an outlet station; a feeding device configured to feed a succession of receptacle closures to the inlet station; a conveyor configured to convey the receptacle closures through the treatment chamber from the inlet station to the outlet station; a sterilization agent injection device configured to inject a sterilization agent into the treatment chamber, wherein: the conveyor includes a plurality of adjacent guide rails; the feeding device is configured to feed the receptacle closures to at least one active guide rail of the plurality of guide rails; and the sterilization agent injection device includes a plurality of injection devices, each injection device being associated with one of the guide rails; and a controller configured to selectively actuate the injection devices according to a first and second operative mode.

20 Claims, 7 Drawing Sheets

(51) Int. Cl.
*A61L 2/22* (2006.01)
*A61L 2/20* (2006.01)
*B65B 55/02* (2006.01)
*B65B 59/00* (2006.01)
*B67B 3/00* (2006.01)
*A61L 2/24* (2006.01)
*B65B 7/28* (2006.01)

(52) U.S. Cl.
CPC .............. *A61L 2/24* (2013.01); *B65B 7/2807* (2013.01); *B65B 55/027* (2013.01); *B65B 59/00* (2013.01); *B67B 3/003* (2013.01); *A61L 2202/122* (2013.01); *A61L 2202/15* (2013.01); *B65B 2210/02* (2013.01)

(56) References Cited

FOREIGN PATENT DOCUMENTS

| | | |
|---|---|---|
| EP | 2687478 A1 | 1/2014 |
| EP | 2318054 B1 | 10/2014 |
| WO | WO 2010/023697 A1 | 3/2010 |
| WO | WO 2010/073064 A1 | 7/2010 |
| WO | WO 2010/128532 A1 | 11/2010 |
| WO | WO 2015/121308 A1 | 8/2015 |

\* cited by examiner

APPARATUS AND METHOD FOR STERILIZING RECEPTACLE CLOSURES

CROSS-REFERENCE TO RELATED APPLICATIONS

This application claims the benefit of priority of European Patent Application No. 16305037.0, filed on Jan. 15, 2016, which is incorporated herein by reference.

TECHNICAL FIELD

The present invention relates to an apparatus and a method for sterilizing receptacle closures, such as screw caps which the following description will refer to, although this is in no way intended to limit the scope of protection as defined by the accompanying claims.

The present invention may be also used to particular advantage for any type/format of receptacle closure, such as differently sized caps, sports caps, stoppers and others.

BACKGROUND ART

The sterilization of packaging material within the food packaging sector is of fundamental interest for guaranteeing the needed shelf life of the packaged food products and, accordingly, the safety of the consumers. This is even more important when food products are packaged under aseptic conditions.

It is known in the art to fill any type of pourable food product such as carbonated liquids (e.g. sparkling water, soft drinks and beer), non-carbonated liquids (including still water, juices, teas, sport drinks, wine, etc) and beverages containing pulps into receptacles, such as containers, vessels, jars and bottles made of base components, like glass, plastics, aluminum, steel, and composites.

In general, the receptacles prior to being filled with the pourable product are sterilized within a receptacle sterilization apparatus and are subsequently filled with the desired pourable product within a filling apparatus.

After the filling of the receptacles, typically the respective pourable product inlets/outlets are sealed by the application and fastening of respective receptacle closures.

Prior to the application of the receptacle closures, the receptacle closures must be sterilized within a respective sterilization apparatus. After sterilization the sterile receptacle closures are fed to a capping device being integrated within the filling apparatus or being separated from the filling apparatus by a filled receptacle conveyor.

Receptacle closures may be of the type known as caps, screw caps, sports caps, stoppers etc., and they may be produced from a variety of materials such as plastics and metal. It is further known that the receptacle closures can vary in format.

In the following, we limit the description to the specific example of plastic screw caps. However, it must be clear that the present invention may be also used to particular advantage for any other type of receptacle closures such as caps, sports caps and others made also from materials different than plastic, such as metal.

A sterilization apparatus for the sterilization of receptacle closures of the same applicant is known from the European patent document EP-B-2318054.

The sterilization apparatus disclosed in EP-B-2318054 comprises a guide rail housed within a treatment chamber designed to receive receptacle closures at an inlet station and to guide the receptacle closures to an outlet station from where the receptacle closures are fed to a capping device.

The sterilization apparatus further comprises a sterilization device having an injection tube arranged below a portion of the guide rail and is adapted to inject a heated and vaporized sterilization agent, in particular heated and vaporized hydrogen peroxide. In particular, one end of the injection tube is arranged in the vicinity of the inlet station and the other end of the injection tube is placed at an intermediate station between the inlet station and the outlet station.

The injection tube has a plurality of injection holes arranged over its complete extension in such that by injection of the heated and vaporized sterilization agent a cloud of sterilization agent is formed within an injection zone of the treatment chamber. In particular, the longitudinal extension of the injection zone is defined by the longitudinal extension of the injection tube.

The sterilization apparatus also comprises a drying device adapted to direct heat air to the receptacle closures in the vicinity of the outlet station for drying off sterilization agent residues from the receptacle closures prior to exiting from the treatment chamber.

The sterilization apparatus disclosed also comprises an exhaust extraction device configured to capture by means of a draught effect, in use, exhaust molecules from the treatment chamber through a plurality of respective exhaust openings. The exhaust extraction device further comprises a plurality of extraction hoods, each associated to one respective exhaust opening. Furthermore, each exhaust hood has flange members for adjusting the effective cross-section of the exhaust hood itself. The adjustment of the effective cross-sections is required for providing on the one hand for the needed exhaust extraction efficiency of the exhaust extraction device and on the other hand to limit the disturbance of the stability of the treatment environment, in particular the cloud of sterilization agent within the injection zone.

One drawback of the sterilization apparatus disclosed in EP-B-2318054 is that the exhaust extraction device requires a sensitive control of the adjustment of the function of the exhaust extraction device comprising the adjustment of the flanges of the exhaust hoods for guaranteeing the stability of the cloud of sterilization agent and, therewith, the quality of the sterilization process.

Furthermore, the disclosure of EP-B-2318054 illustrates that the guide rail guides receptacle closures of only one type/format of receptacle closures. Thus, in case of a change to types/formats of receptacle closures not supported by the guide rail extensive and time consuming changes need to be performed to adapt the sterilization apparatus to the new closure format.

DISCLOSURE OF INVENTION

It is therefore an object of the present invention to provide a sterilization apparatus and a method to overcome, in a straightforward and low-cost manner, the aforementioned drawbacks.

According to the present invention, there is provided a sterilization apparatus as claimed in claim 1.

According to the present invention, there is further provided a method as claimed in claim 11.

According to the present invention, there is also provided a sterilization apparatus according to claim 15.

BRIEF DESCRIPTION OF THE DRAWINGS

A non-limiting embodiment of the present invention will be described by way of example with reference to the accompanying drawings, in which.

BEST MODES FOR CARRYING OUT THE INVENTION

Figure 1:
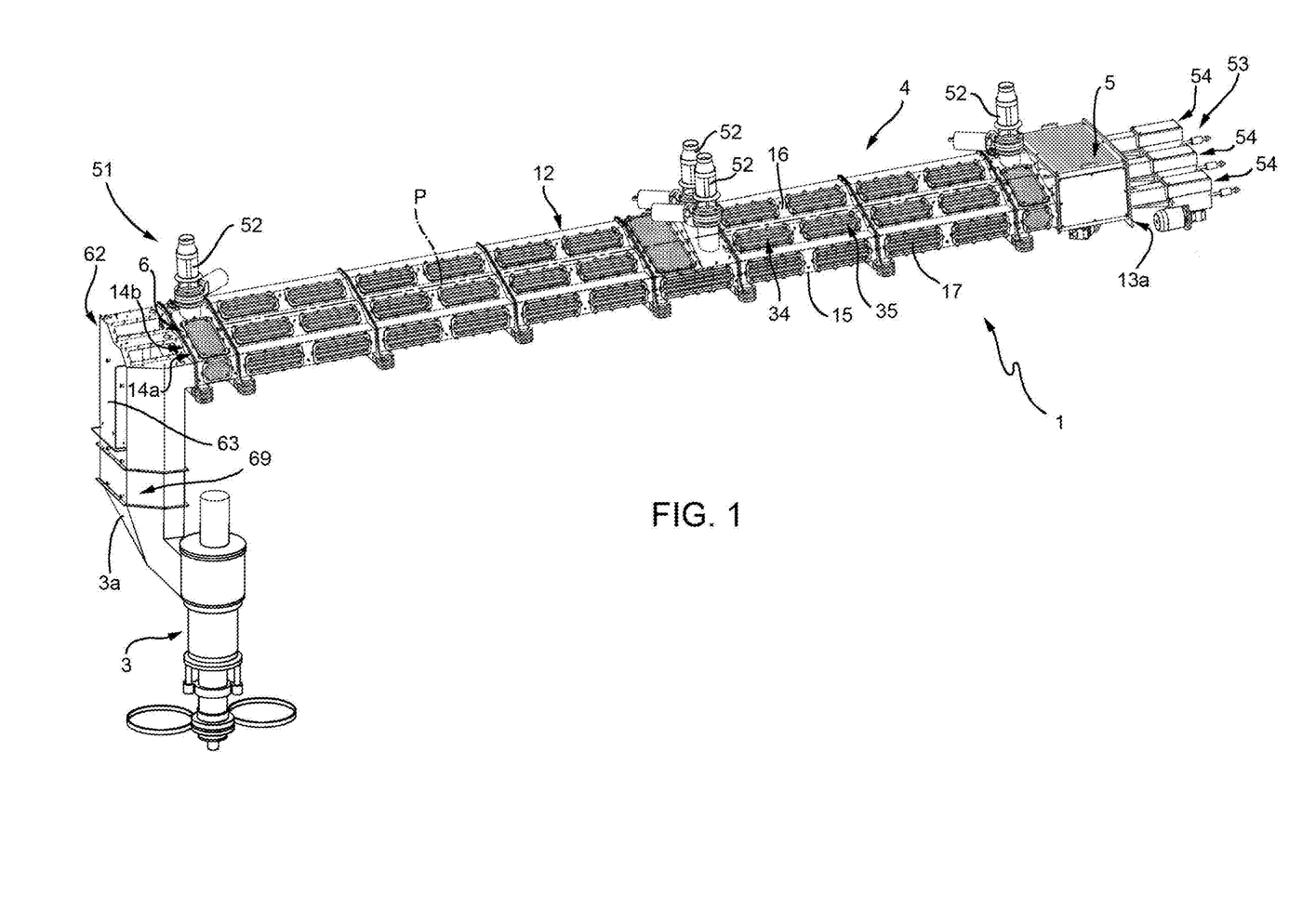
FIG. 1 shows a perspective view of a sterilization apparatus according to the present invention connected to a capping device, with parts removed for clarity.

Number 1 in FIG. 1 indicates as a whole a sterilization apparatus apt to sterilize receptacle closures 2, in particular prior to being fed to a capping device 3.

Figures 2, 7:
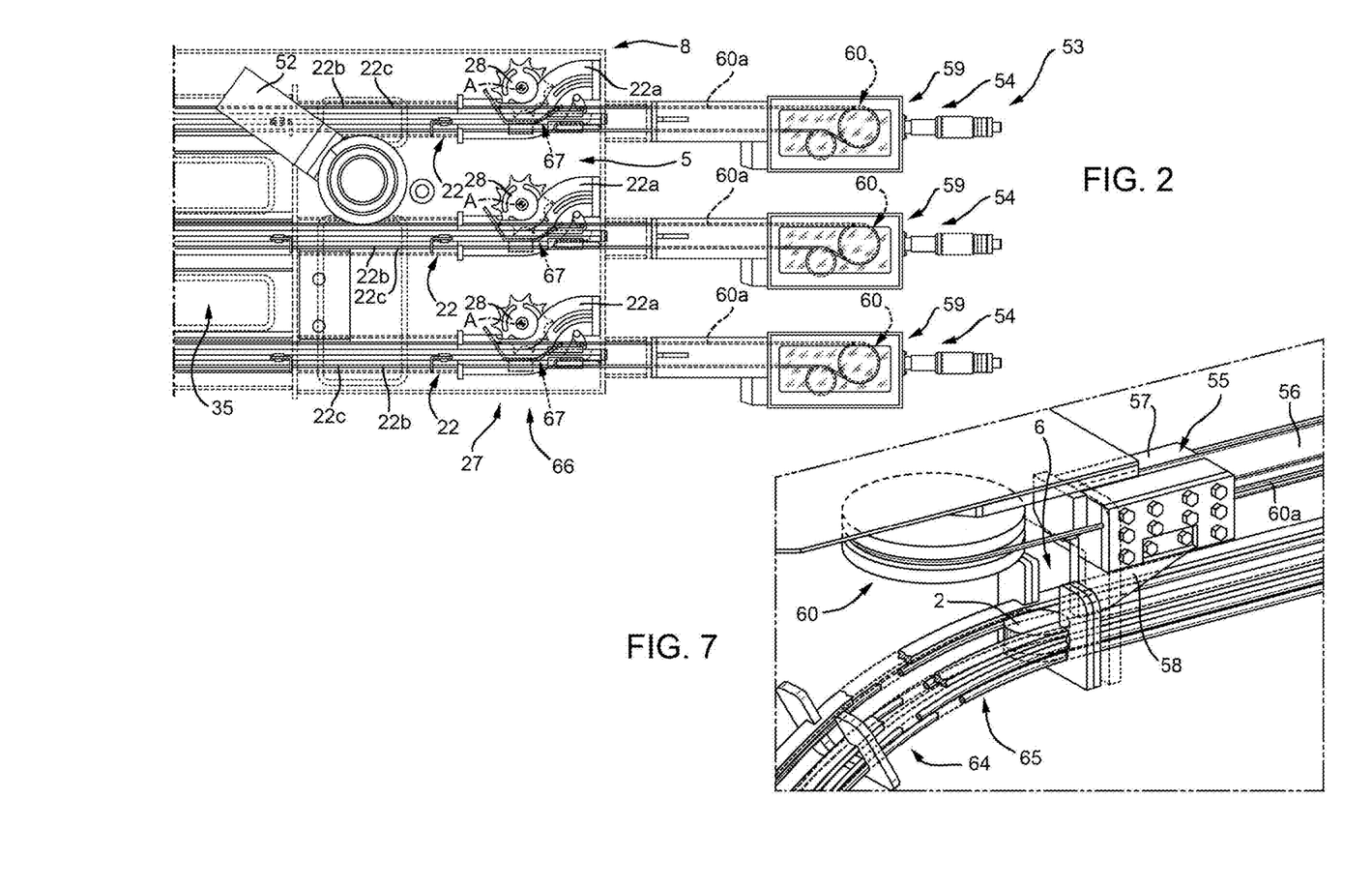
FIG. 2 shows a larger-scale top view of a first portion of the apparatus of FIG. 1, with parts removed for clarity.
FIG. 7 shows a perspective view of a third portion of the apparatus of FIG. 1, with parts removed for clarity.
Figure 3:
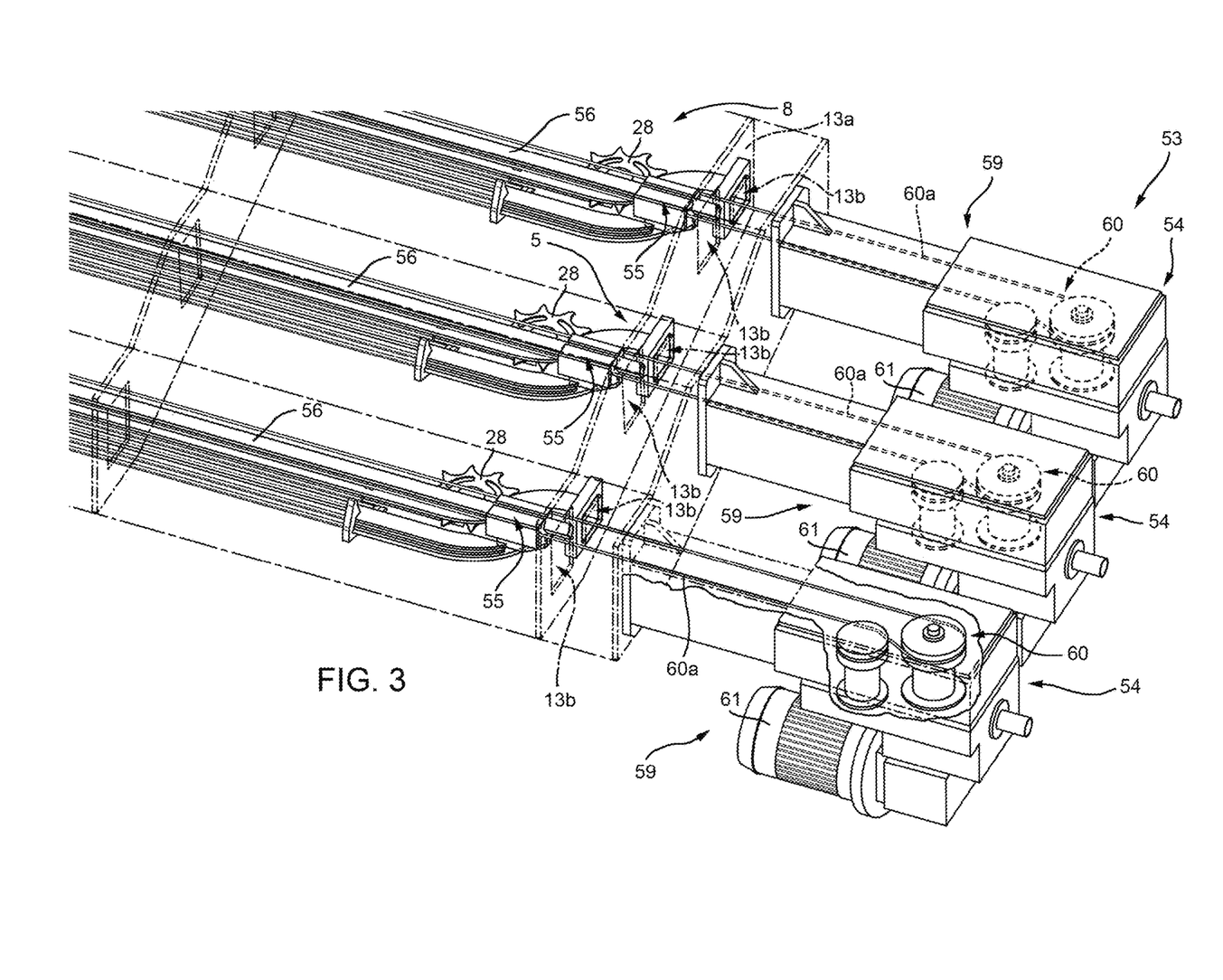
FIG. 3 shows a larger-scale top perspective view of the first portion of FIG. 2, with parts removed for clarity.

With particular reference to FIGS. 1, 2 and 3 apparatus 1 comprises:
- a treatment chamber 4 having an inlet station 5 and an outlet station 6;
- feeding means (known as such and not shown) apt to feed a succession of receptacle closures 2 to the inlet station 5;
- conveying means 8 apt to convey the receptacle closures 2 through the treatment chamber 4 from the inlet station 5 to the outlet station 6; and
- sterilization agent injection means 9 adapted to inject a sterilization agent into treatment chamber 4 for applying a sterilization agent to the receptacle closures 2 being advanced from inlet station 5 to outlet station 6.

Figure 5:
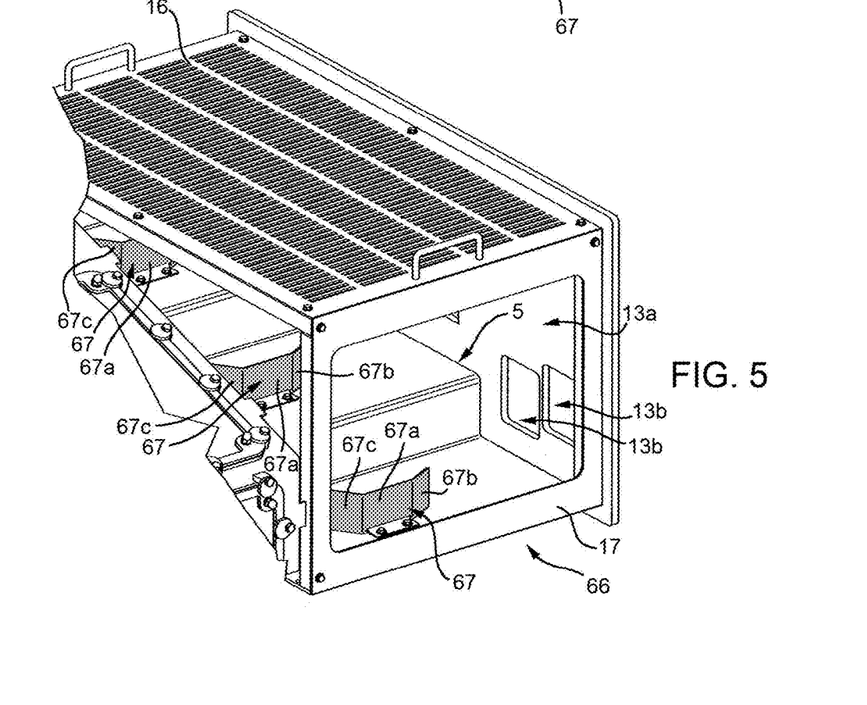
FIG. 5 shows an enlarged lateral perspective view of another detail of the first portion of FIGS. 2 and 3.
Figure 6:
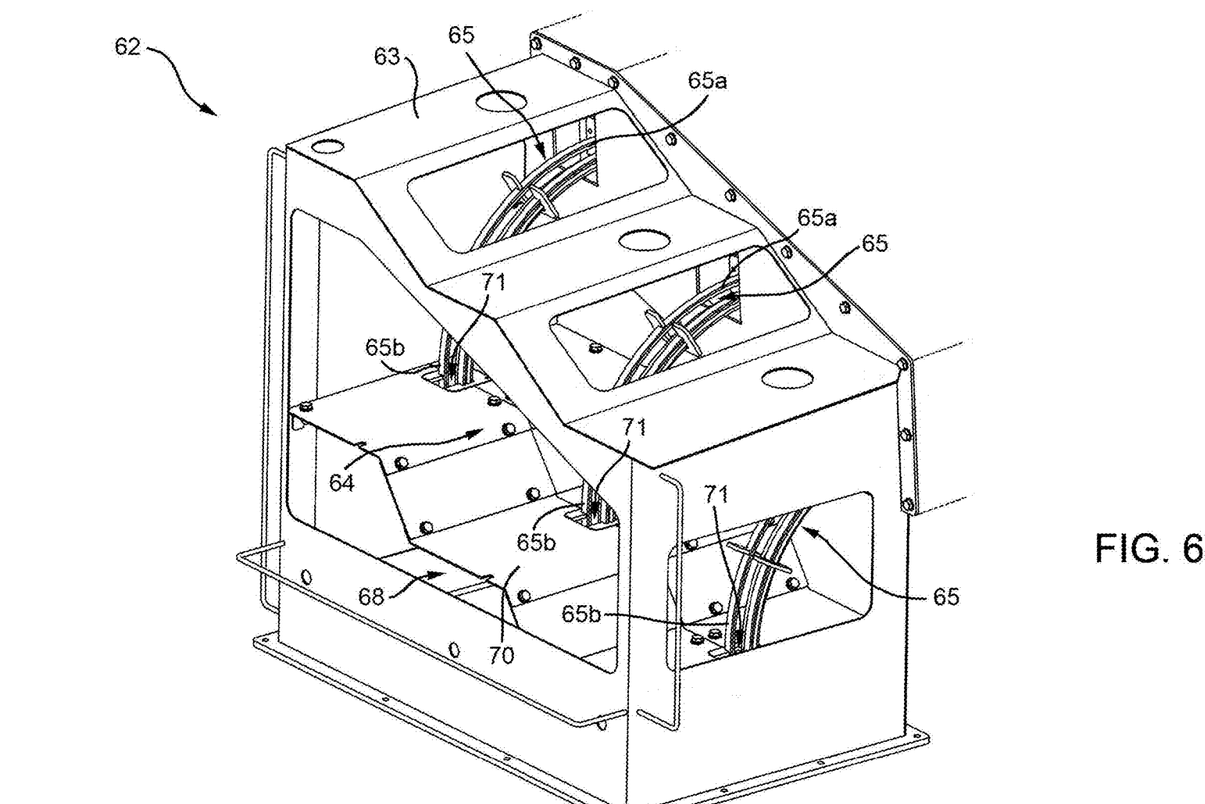
FIG. 6 shows a perspective view of a second portion of the apparatus of FIG. 1.

In more detail, with particular reference to FIGS. 1, 5 and 6, treatment chamber 4 defines a treatment environment within which receptacle closures 2 are to be sterilized. Treatment chamber 4 has a substantially parallelepiped configuration with a substantially horizontal orientation. In particular, treatment chamber 4 is delimited by an outer shell 12. Shell 12 comprises an inlet wall 13a and an outlet wall 14a in the area of inlet station 5 and outlet station 6, respectively. Furthermore, shell 12 of treatment chamber 4 has a bottom wall 15, a top wall 16 and lateral side walls 17.

In more detail, inlet wall 13a has a plurality of inlet openings 13b and outlet wall 14a has a plurality of outlet openings 14b.

In particular, a fraction of said inlet openings 13b is designed to allow for feeding of the receptacle closures 2 through said respective fraction of inlet openings 13b by the feeding means into treatment chamber 4. The function of the other fraction of inlet openings 13b will be explained further below in the description. Additionally, outlet openings 14a are configured for allowing to discharge receptacle closures 2 out of treatment chamber 4.

With particular reference to FIGS. 2 to 5 and 7 to 9, conveying means 8 comprise a plurality of adjacent guide rails 22, in the specific example of this embodiment three, each one configured to receive the succession of receptacle closures 2 from the feeding means and to carry and guide said receptacle closures 2 along a path P from the inlet station 5 to outlet station 6.

In particular, guide rails 22 are parallel to each other and, more particularly guide rails 22 are laterally separated from each other. More specifically, two guide rails 22 are placed at relative external portions of treatment chamber 4 and the third guide rail 22 is arranged at a central portion within treatment chamber 4 between the externally positioned guide rails 22.

More specifically, each guide rail 22 is adapted to receive, carry and guide receptacle closures 2 of one relative type/format of respective closures or one respective group of types/formats of receptacle closures. Preferably, each guide rail 22 is adapted to handle one relative type/format of receptacle closures or one relative group of types/formats of receptacle closures different from the ones of the other guide rails 22.

Furthermore, each guide rail 22 is arranged within treatment chamber 4 between inlet station 5 and outlet station 6. More specifically, each guide rail 22 has one end placed in the proximity of one respective inlet opening 13b and another end in the vicinity of one respective outlet opening 14b.

Additionally, each guide rail 22 has a substantially horizontal orientation and is configured to guide receptacle closures 2 along path P, in particular with the respective closure cavities 2a facing bottom wall 15 of treatment chamber 4; i.e. the respective closure cavities 2a of receptacle closures 2 point downwards.

In more detail, each guide rail 22 has a curved inlet portion 22a arranged in the area of inlet station 5 and configured to receive the receptacle closures 2 from the feeding means and a main rectilinear portion 22b connected to curved inlet portion 22a and extending towards outlet station 6 and configured to receive the receptacle closures 2 from inlet portion 22a.

In even more detail, each guide rail 13 comprises a plurality of guide bars 23, in the specific example four, for supporting the receptacle closures 2 within a respective guiding space 24 delimited by the guide bars 22 themselves.

Each guide rail 22 also comprises a support assembly 25 having a plurality of support elements 26 for supporting guide bars 22.

In more detail, the feeding means are configured to feed the receptacle closures 2 to at least one active guide rail 22 of the plurality of guide rails 22. Preferably, in use, the feeding means feed receptacle closures 2 of one specific type/format of receptacle closures to the guide rail 22 being adapted to receive, carry and guide the specific type/format of receptacle closures.

In particular, feeding means comprise air flow generating means designed to feed the succession of receptacle closures 2 to inlet station 5 by a flow of air. In particular, the flow of air feeds the receptacle closures 2, in particular through the respective inlet opening 13b, to the respective inlet portions 22a of guide rails 22.

Alternatively, feeding means could comprise a mechanical feeding mechanism.

With particular reference to FIGS. 2 to 5 and 8, conveying means 8 further comprise actuating means 27 apt to direct the receptacle closures 2 from inlet station 5 to outlet station 6.

In more detail, actuating means 27 comprise a plurality of directing and pushing devices, in particular motor-driven star wheels 28, in the specific example three, each one associated to one respective guide rail 22 and configured to direct and push the receptacle closures 2 received, carried and guided by the respective guide rail 22 towards outlet station 6.

In particular, each star wheel 28 is placed in the area of inlet station 5 adjacent to the respective guide rail 22, in particular adjacent to curved inlet portion 22a and main rectilinear portion 22b and is rotatable around a rotation axis A perpendicular to guide rails 22.

Each star wheel 28 is configured to cooperate with the succession of receptacle closures 2 fed by the feeding means to the respective guide rail 22. In particular, each star wheel 28 is apt to actuate the advancement of the succession of receptacle closures 2 from inlet station 5 to outlet station 6. In particular, each star wheel 28 is designed to push, at least indirectly, the succession of receptacle closures 2 fed to the respective guide rail 22 along path P from inlet station 5 to outlet station 6.

Furthermore, each guide rail 22 and the respective star wheel 28 are supported on bottom wall 15.

Figures 8, 9:
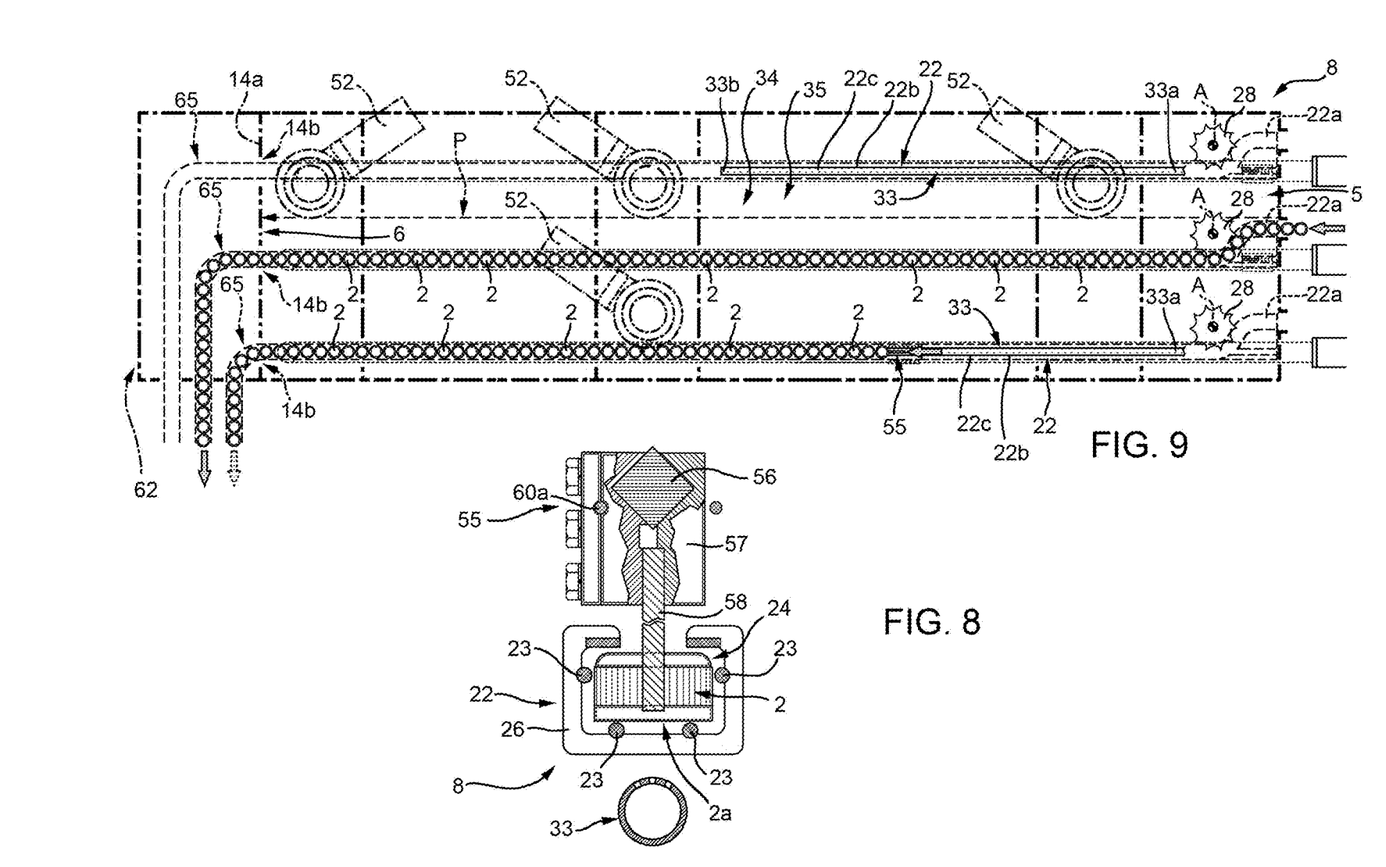
FIG. 8 shows a sectioned view of a fourth portion of the apparatus of FIG. 1, with parts removed for clarity.
FIG. 9 shows a top view of the apparatus of FIG. 1 illustrating different operation conditions of the apparatus, with parts removed for clarity.
Figure 10:
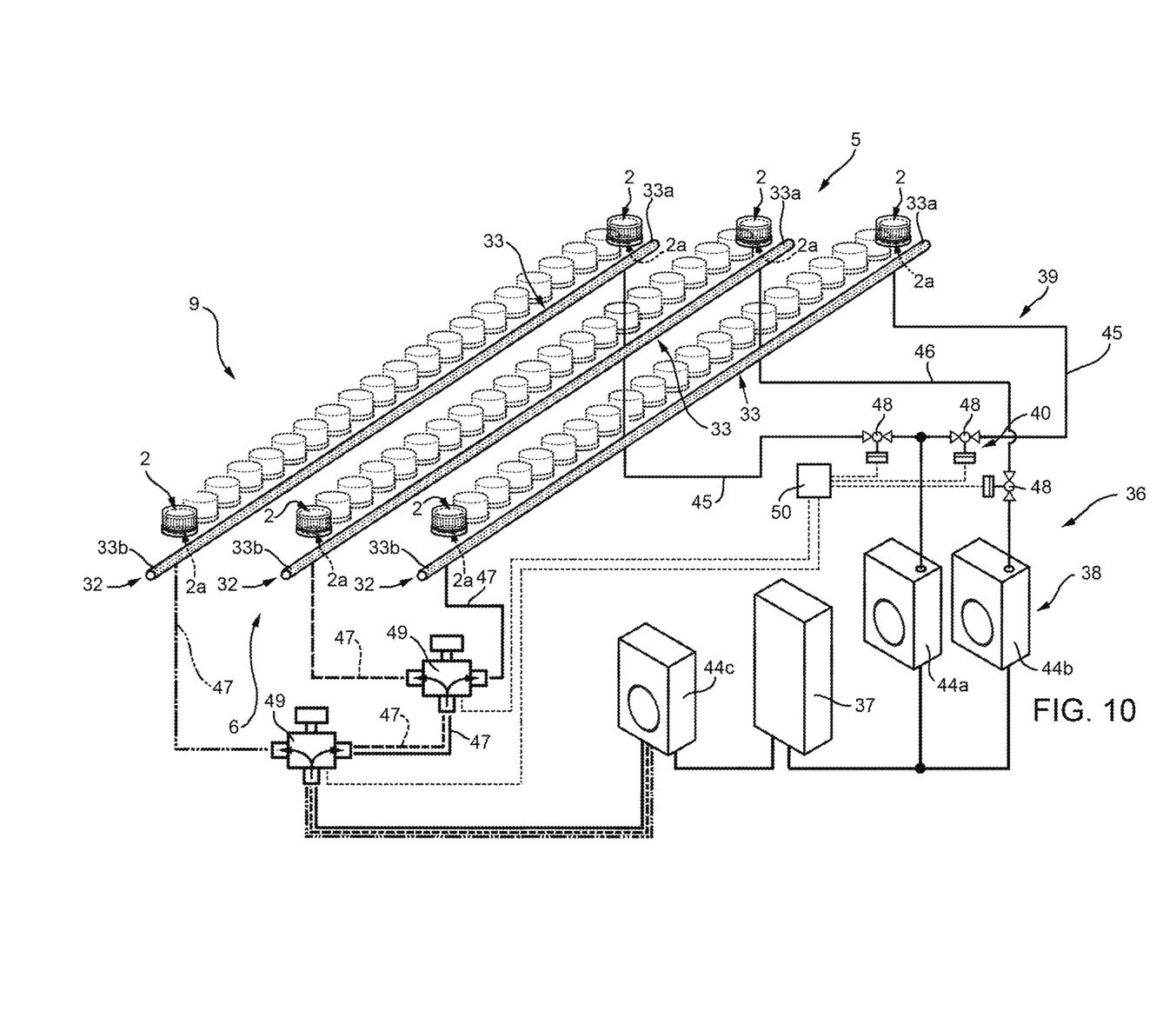
FIG. 10 shows a schematic perspective view of a sterilization agent distributor unit of the apparatus of FIG. 1.

With particular reference to FIGS. 8 to 10, sterilization injection means 9 comprise a plurality of injection devices 32, in the specific embodiment disclosed three, associated to each one of guide rails 22. In particular, each injection device 32 is associated to one respective guide rail 22.

Each injection device 32 is configured to inject the sterilization agent, preferably hydrogen peroxide, or peracetic acid, in particular in heated and vaporized form into treatment chamber 4, in particular towards the respective guide rail 22.

In more detail, each injection device 32 comprises at least one injection tube 33 arranged adjacent to the respective guide rail 22 and extending along at least an injection portion 22c of the respective guide rail 22, in particular the respective main rectilinear portion 22b. In particular, each injection tube 33 extends from within the proximity of inlet station 5 towards an intermediate station 34 being positioned between inlet station 5 and outlet station 6.

More specifically, each injection tube 33 is arranged below the respective guide rail 22. Accordingly, in use, the respective cavities 2a of receptacle closures 2 carried and guided by the respective active guide rail 22 face, along injection portion 22c, the respective injection tube 33.

Furthermore, each injection tube 33 is mounted to the respective guide rail 22, in particular the respective support assembly 25.

Additionally, according to the arrangement of the guide rails 22 two injection tubes 33 are arranged at the relative external portions within treatment chamber 4 and the other injection tube 33 is positioned along the centered portion within treatment chamber 4.

Furthermore, each injection tube 33 comprises a plurality of injection holes adapted to release the sterilization agent into treatment chamber 4.

In particular, in use, through injection of the sterilization agent a cloud of sterilization agent develops within the treatment environment, in particular within an injection zone 35 of treatment chamber 4.

In particular, the longitudinal extension of each injection tube 33 substantially defines the longitudinal extension of injection zone 35. Thus, the longitudinal extension of injection zone 35 substantially extends from the proximity of inlet station 5 to the proximity of intermediate station 34.

Sterilization agent injection means 9 further comprise a sterilization agent distributor 36 adapted to selectively supply the sterilization agent to injection devices 32, in particular to the respective injection tubes 33. More specifically, the sterilization agent distributor 36 is apt to selectively supply the sterilization agent to a first end portion 33a and/or to a second end portion 33b of each injection tube 33. In particular, the respective first end portion 33a of each injection tube 33 is positioned in the proximity of inlet station 5; and the respective second end portion 33b of each injection tube 33 is arranged in the vicinity of intermediate station 34.

With particular reference to FIG. 10, sterilization agent distributor 36 comprises:
  a sterilization agent tank 37 containing the sterilization agent;
  a sterilization agent conditioning device 38 adapted to receive the sterilization agent from sterilization agent tank 37 and being configured to prepare, in particular heat and vaporize the sterilization agent;
  a conduit assembly 39 configured to establish a fluid connection between sterilization agent conditioning device 38 and the one or more injection devices 32, in particular the injection tubes 33; and
  a valve assembly 40 adapted to selectively control the fluid connection between sterilization agent conditioning device 38 and the one or more injection devices 32, in particular the injection tubes 33.

In more detail, sterilization agent conditioning device 38 comprises one or more conditioning units 44a, 44b, 44c, in the specific example of FIG. 10 three, each being configured to receive the sterilization agent from sterilization tank 37 and being configured to heat and vaporize the sterilization agent in a known manner and to feed the heated and vaporized sterilization agent to injection tubes 33.

Conduit assembly 39 comprises:
  first conduits 45 configured to establish a fluid connection between conditioning unit 44a and two injection tubes 33, in particular these two injection tubes 33 being placed along the relative external portions;
  a second conduit 46 apt to establish a fluid connection between conditioning unit 44b and the injection tube 33 not being fluidically connected to conditioning unit 44a, in particular the injection tube 33 arranged along the central portion; and
  third conduits 47 configured to establish a fluid connection between injection tubes 33 and conditioning unit 44c.

In particular, first conduits 45 and second conduit 46 are designed to cooperate with the first end portions 33a of the respective injection tubes 33 for establishing the fluid connection between the relative conditioning unit 44a or 44b and the respective injection tubes 33 through the respective end portions 33a. Third conduits 47 are designed to cooperate with the second end portions 33b of the injection tubes 33 for establishing the fluid connection between conditioning unit 44c and the injection tubes 33 through the respective second end portions 33b.

Valve assembly 40 comprises:
  a plurality of first valve members 48, in the specific example of FIG. 10 three, each one associated to one respective injection tube 33, arranged between the respective injection tube 33 and the relative conditioning unit 44a or 44b and configured to open or close the fluid connection between the respective injection tube 33 and conditioning unit 44a or 44b; and
  a plurality of second valve members 49 interposed between conditioning unit 44c and the injection tubes 33 and configured to selectively open or close the fluid connection between conditioning unit 44c and injection tubes 33.

More specifically, first valve members 48 are configured to selectively open or close the fluid connection between the respective conditioning unit 44a or 44b and the injection tubes 33 through the respective first end portions 33a and second valve members 49 are apt to selectively open or close the fluid connection between conditioning unit 44c and the injection tubes 33 through the respective second end portions 33b.

Furthermore, apparatus 1 further comprises control means 50, in particular associated to sterilization agent injection means 9, adapted to control sterilization agent distributor 36 and, accordingly injection devices 32.

More specifically, control means 50 are configured to selectively actuate the injection devices 32 according to a first and a second operative mode:
in the first operative mode, control means 50 are configured to actuate the injection devices 32 associated to the active guide rail 22 (i.e. the guide rail 22 guiding the receptacle closures 2 from inlet station 5 to outlet station 6); and
in the second operative mode, control means 50 are configured to actuate the injection device 32 associated to the active guide rail 22 and to actuate the injection devices 32 of one or more guide rails 22 adjacent to the active guide rail 22 itself.

More specifically, control means 50 are configured to control sterilization agent distributor 36 to selectively supply the sterilization agent to injection devices 32, in particular to injection tubes 33 and even more particularly to injections tubes 33 through the respective first end portions 33a and to the respective second end portions 33b of injection tubes 33.

In particular, in the first operative mode sterilization agent distributor 36 is controlled to supply the sterilization agent to the respective injection tube 33 associated to the active guide rail 22 through the first and second end portion 33a, 33b; and
in the second operative mode the sterilization agent distributor 36 is controlled to supply the sterilization agent to the respective injection tube 33 associated to the active guide rail 22, in particular through the respective first and second end portions 33a, 33b and to the respective injection tube 33 or injection tubes 33 of one or more guide rails 22 adjacent to the active guide rail 22 itself, in particular through the respective first end portions 33a.

Even more specifically, in the first operative mode control means 50 are configured to open the respective first valve member 48 of the respective injection tube of the active guide rail 22 for establishing the fluid connection with the respective conditioning unit 44a or 44b; and to control the respective second valve member 49 or the respective second valve members 49 for establishing the fluid connection between the respective injection tube 33 of the active guide rail 22 and the conditioning unit 44c.

In the second operative mode control means 50 are adapted to open the respective first valve member 48 of the respective injection tube 33 of the active guide rail 22 for establishing the fluid connection with the respective conditioning unit 44a or 44b; and to control the respective second valve member 49 or the respective second valve members 49 for establishing the fluid connection between the respective injection tube 33 of the active guide rail 22 and the conditioning unit 44c and to open the respective first valve 48 or the respective first valves 48 of the respective injection tube 33 or of the respective injection tubes 33 of one or more guide rails 22 adjacent to the active guide rail 22.

With reference to FIGS. 1, 2 and 9, apparatus 1 comprises exhaust extraction means 51 configured to receive and extract exhaust molecules forming during the sterilization of receptacle closures 2 within treatment chamber 4.

More specifically, exhaust extraction means 51 comprise:
a suction unit (not shown and known as such) for generating suction force and for collecting the exhaust molecules; and
a plurality of extraction hoods 52 mounted to treatment chamber 4 and fluidically connected to the suction unit and configured to receive the exhaust molecules from inside of the treatment chamber 4.

In particular, in the specific example described, exhaust extraction means 51 comprise four extraction hoods 52. One extraction hood 52 is arranged in the proximity of inlet station 5, another one in the area of outlet station 6 and the remaining two extraction hoods 52 are positioned in the vicinity of intermediate station 34. Preferably, the hoods 52 may have a telescopic configuration for adjusting the know draught effect.

Apparatus 1 further comprises drying means (not shown and known as such) adapted to dry off the sterilization agent from receptacle closures 2. More specifically, the drying means are designed to direct heated air into treatment chamber 4 in the area of outlet station 6 for removing sterilization agent residues from the receptacle closures 2 moving to outlet station 6 and prior to exiting treatment chamber 4.

Apparatus 1 also comprises heating means (not shown and known as such) apt to heat treatment chamber 4 for defining the temperature within treatment chamber 4 itself. In particular, the heating means comprise a plurality of electrical heating members (not shown and known as such), in particular mounted to shell 12 of treatment chamber 4 at varying portions of treatment chamber 4 and each one being selectively controllable.

In particular, the temperature in the area of injection zone 35 is determined by the action of the heating means and the temperature of the heated and vaporized sterilization agent injected into treatment chamber 4 by sterilization agent injection means 9.

Additionally, the temperature in the proximity of outlet station 6 is determined by the action of the heating means and the heated air introduced into treatment chamber 4 by the drying means.

With particular reference to FIGS. 2 to 4 and 7 to 9, apparatus 1 comprises expelling means 53 configured to advance the succession of receptacle closures 2 along path P towards outlet station 6, in particular for expelling receptacle closures 2 from active guide rail 22, in particular out of treatment chamber 4.

In particular, expelling means 53 are designed to be actuated after deactivation of the feeding means. Accordingly, expelling means are configured to be actuated after interruption of the feeding of receptacle closures 2 to inlet station 5.

In more detail, expelling means 53 comprise a plurality of expelling devices 54, in the particular example three, each one associated to one respective guide rail 22 and adapted to advance receptacle closures 2 received, carried and guided by the respective guide rail 22 along the respective guide rail 22 to outlet station 6.

Each expelling device 54 has an interaction assembly 55 configured to cooperate with receptacle closures 2 received, carried and guided by the respective guide rail 22 for advancing said receptacle closures 2 to outlet station 6.

Furthermore, interaction assembly 55 is designed to be actuated to move from a rest position in the vicinity of inlet station 5 to outlet station 6 for expelling receptacle closures 2 from the respective guide rail 22; and to be actuated to move from outlet station 6 back to its rest position.

Each expelling device 54 further comprises a guide beam 56 arranged adjacent to, in particular parallel to and above the respective guide rail 22 substantially extending from inlet station 5 to outlet station 6 and designed to moveably support the respective interaction assembly 55.

More specifically, each interaction assembly 55 comprises a slide member 57 moveably mounted to the respective guide beam 56 and an interaction element 58 fixed to said slide member 57 and apt to contact the receptacle closures 2 and to move the receptacle closures 2 to outlet station 6 during movement of the respective interaction assembly 55 towards outlet station 6 itself.

Furthermore, each expelling device 55 has an actuation assembly 59 apt to drive each interaction assembly 55, in particular the respective slide member 57 from the respective rest position to outlet station 6 and from outlet station 6 back to the respective rest position.

Each actuation assembly 59 has a respective conveyor pulley 60 having a belt 60a and a driving motor 61. In particular, each belt 60a extends through inlet wall 13a. In particular, each belt 60a extends through one respective inlet opening 13b of the fraction of inlet openings 13b not used for feeding of receptacle closures 2 to inlet station 5.

The respective interaction assembly 55, in particular the slide member 57 is coupled to the respective belt 60a. Thus, each actuation assembly 59 is configured to actuate movement of the respective interaction assembly 55, in particular the slide member 57 by driving of the respective belt 60a.

With reference to FIGS. 1 and 6, apparatus 1 further comprises an outlet unit 62 adapted to receive sterilized receptacle closures 2 from conveying means 8, in particular in the area of outlet station 6. Furthermore, outlet unit 62 is configured to feed the sterilized receptacle closures 2 to capping device 3.

Outlet unit 62 comprises:
  an outlet chamber 63 mounted to treatment chamber 4, in particular in the proximity of outlet station 6; and designed to delimit an outlet space 64; and
  a plurality of outlet rails 65, in the specific example three, placed within outlet chamber 63 and configured to receive sterilized receptacle closures 2 from guide rails 22.

Outlet chamber 63 is further connected to an entrance portion 3a of capping device 3.

In more detail, each outlet rail 65 is connected to one respective guide rail 22 and is apt to receive sterilized receptacle closures 2 from the respective guide rail 22. Each outlet rail 65 is also adapted to guide the sterilized receptacle closures 2 to capping device 3, in particular to entrance portion 3a.

Furthermore, each outlet rail 65 comprises a curved portion 65a connected to the respective guide rail 22 and a rectilinear portion 65b extending from curved portion 65a towards capping device 3.

Each outlet rail 65 substantially has a structure similar to the structure of the respective guide rail 22. Thus, each outlet rail 65 is adapted to receive the same relative type/format or the same relative group of types/formats of receptacle closures as the respective guide rail 22.

Figure 4:
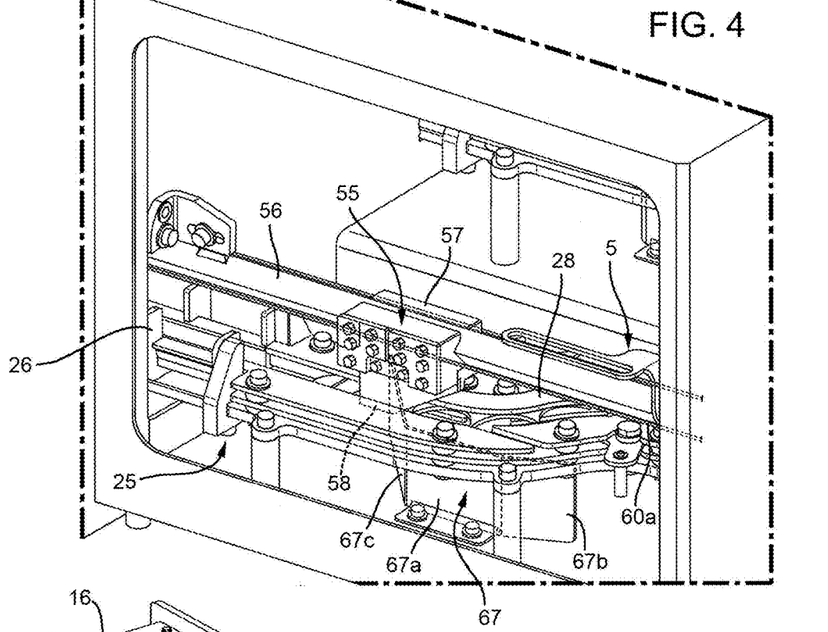
FIG. 4 shows a larger-scale lateral perspective view of a detail of the first portion of FIGS. 2 and 3, with parts removed for clarity.

With reference to FIGS. 2, 4 and 5, apparatus 1 further comprises deflector means 66 arranged in the area of the inlet station 5 and being configured to restrict the flow of air generated by the air flow generating means of the feeding means within the area of inlet station 5. In particular, deflector means 66 are adapted to enhance the stability of the treatment environment, in particular the cloud of sterilization agent within treatment chamber 4.

Deflector means 66 comprise a plurality of deflector plates 67, each one associated to one respective guide rail 22.

Each deflector plate 67 is positioned below the respective guide rail 22, in particular adjacent to the respective inlet portion 22a and the respective main portion 22b of the respective guide rail 22.

Each deflector plate 67 comprises a main plate portion 67a, in particular parallel to the respective main portion 22b of the respective guide rail 22. Each deflector plate 67 further has a first and second angled plate portion 67b and 67c angled with respect to main plate portion 67a and, in particular diverging from opposite side edges of main plate portion 67a. More specifically, plate portion 67b is positioned in the area of inlet station 5 and is apt to direct the flow of air towards second angled plate portion 67c. Plate portion 67c is designed to block the propagation of the flow of air into a direction towards outlet station 6, in particular parallel to rectilinear main portion 22b of the respective guide rail 22. Overall, deflector plate 67, in particular by cooperation of main plate portion 67a and first and second plate portion 67b and 67c is configured to swirl the flow of air within the area of inlet station 5.

Furthermore, each deflector plate 67 is mounted to bottom plate 15.

With reference to FIGS. 1 and 6, apparatus 1 further comprises air shielding means 68 configured to hinder entrance of air from an outside space 69 into treatment chamber 4 from the area of the outlet station 6. Additionally, air shielding means 68 are apt to enhance stability of the treatment environment, in particular the cloud of sterilization agent within treatment chamber 4, more specifically by hindering air to enter from the area of the outlet station 6 as otherwise entrance of air would disturb the treatment environment.

More specifically, air shielding means 68 comprise a shielding plate 70 arranged inside of outlet chamber 63 and having a plurality of openings 71, each one associated to one respective outlet rail 65.

In particular, each outlet rail 65 extends through the respective opening 71 within shielding plate 70. More particularly, each opening 71 has a substantially rectangular configuration.

Furthermore, in this particular embodiment, outside space 60 is defined by entrance portion 3a of capping device 3 which is in fluidic connection with outlet chamber 63. More specifically, entrance portion 3a is provided with an overpressurized air environment. Thus, in this specific embodiment, air shielding means 68, in particular shielding plate 70 is designed to hinder the overpressurized air to enter treatment chamber 4.

It must be understood, that deflector means 66 and/or air shielding means 68 can be used in an alternative sterilization apparatus (not shown) having one single guide rail 22 and one respective single injection device 22.

In use, the feeding means of apparatus 1 feed a plurality of receptacle closures 2, in particular by means of a flow of air, to inlet station 5 of treatment chamber 4. In particular, the succession of receptacle closures 2 is fed to at least one active guide rail 22 of the plurality of guide rails 22. In particular, the feeding means feed a succession of receptacle closures 2 of one specific type/format of receptacle closures to one respective active guide rail 22 of the plurality of guide rails 22, in particular the respective guide rail adapted to receive, carry and guide the specific type/format of receptacle closures.

Then, the receptacle closures 2 are advanced from inlet station 5 to outlet station 6. In particular, in the area of inlet station 5 the respective star wheel 28 of the active guide rail 22 rotating around axis A starts to interact with the receptacle closures 2 fed to the active guide rail 22 and directs the receptacle closures 2 to outlet station 6 (see FIG. 9 illustrating this case in the example of the guide rail 22 arranged along the central portion within treatment chamber 4).

In particular, at first the respective star wheel 28 directs the receptacle closures 2 from curved inlet portion 22a to rectilinear main portion 22b. Then, the respective star wheel 28 indirectly pushes the receptacle closures 2 being carried and guided by the respective rectilinear main portion 22b to outlet station 6 by directly advancing a limited number of receptacle closures 2 and the pushing of neighboring receptacle closures 2.

During advancement of the receptacle closures 2 towards outlet station 6 injection devices 32 are selectively actuated according to a first and second operative mode:

in the first operative mode, the respective injection device 32 associated to the active guide rail 22 is activated; and in the second operative mode, the respective injection device 32 associated to the active guide rail 22 and the respective injection devices 32 of one or more guide rails 22 adjacent to the active guide rail 22 are activated.

In more detail, in the first operative mode, the sterilization agent is supplied to the respective injection tube 33 of the respective injection device 32 of active guide rail 22, in particular through the respective first and second end portions 33a, 33b of the relative injection tube 33.

In the second operative mode, the sterilization agent is supplied to the respective injection tube 33 of the respective injection device 32 of active guide rail 22, in particular through the respective first and second end portions 33a, 33b of the relative injection tube 33. Furthermore, the sterilization agent is supplied to one or more guide rails 22 neighbored to the active guide rail 22, preferably to the respective first end portions 33a.

The respective injection tube 33 of the active guide rail 22 injects the sterilization agent towards the cavities 2a of the receptacle closures 2 and the respective injection tube 33 of the neighboring guide rails 22 inject the sterilization agent towards the outside of the receptacle closures 2. Overall, a stable cloud of the sterilization agent is generated.

Deflector means 66 hinder the flow of air used for feeding the receptacle closures 2 to inlet station 5 to disturb the stability of the treatment environment, in particular the cloud of the sterilization agent. In particular, deflector means 66 or more particularly the respective deflector plates 67 restrict the flow of air generated by the air flow generating means within the area of the inlet station 5.

Overall, receptacle closures 2 advancing from inlet station 5 to outlet station 6 pass at first through the cloud of sterilization agent being present within the injection zone 35 of treatment chamber 4. Thereby, the sterilization agent deposits on the receptacle closures 2, which during further advancement the sterilization agent sterilizes the receptacle closures 2. Upon even further advancement residues of the sterilization agent remaining on the receptacle closures 2 are dried off from the receptacle closures 2, in particular by treatment with heated air by actuation of the drying means. In particular, the residues of the sterilization agent are dried off in the vicinity of outlet station 6, i.e. immediately prior to exiting treatment chamber 4.

Then, the sterilized receptacle closures 2 are moved out of treatment chamber 4. In particular, the receptacle closures 2 are fed to the respective outlet rail 65. Then, the sterilized receptacle closures 2 are fed to capping device 3.

In case, the feeding of further receptacle closures 2 is interrupted, advancement of receptacle closures 2 from inlet station 5 to outlet station 6 is not further possible by actuation through actuating means 27, as the respective star wheel 28 cannot indirectly advance the receptacle closures 2 anymore. At this point, expelling means 53 are actuated. In particular, expelling means 53 expel receptacle closure 2 from the active guide rail (22) after interruption of feeding the receptacle closures (2) to the active guide rail (22) itself (see FIG. 9 illustrating this case in the example of the guide rail 22 arranged along one of the external portions within treatment chamber 4). More specifically, the respective expelling device 54 of the active guide rail 22 moves receptacle closures 2 to outlet station 6.

The advantages of apparatus 1 according to the present invention will be clear from the foregoing description.

In particular, sterilization apparatus 1 allows to quickly changing the format of the receptacle closures 2 by providing a plurality of guide rails 22, each of which being designed to receive, carry and guide one respective type/format of receptacle closures or to receive and guide a relative group of types/formats of receptacle closures.

A further advantage is that the cloud of sterilization agent develops in the second operative mode thanks to the injection of the sterilization agent from at least two injection devices 32, in particular the respective injection device 32 of the active guide rail 22 and one or two injection devices 32 of the neighboring guide rails 22, leading to a stable cloud of sterilization agent which is less sensitive to the extraction of exhaust molecules by the exhaust extraction means 51.

An even further advantage is that the sterilization apparatus 1 provides for deflector means 66 and air shielding means 68 leading to a further enhancing the stability of the cloud of sterilization agent.

Clearly, changes may be made to apparatus 1 as described herein without, however, departing from the scope of protection as defined in the accompanying claims.

The invention claimed is:

1. A cap sterilization apparatus for sterilizing caps, comprising:
 a treatment chamber having an inlet station;
 a cap feeder configured to feed a succession of caps to the inlet station;
 a conveyor configured to convey the caps through the treatment chamber from the inlet station to an outlet station, the conveyor including;
  a plurality of substantially horizontal guide rails, including:
   at least one first guide rail configured to carry and guide caps having a first format; and
   at least one second guide rail located adjacent to the first guide rail and configured to carry and guide caps having a second format different from the first format; and
  a plurality of pushing devices, each pushing device being selectively activatable for pushing the caps along one of the first and second guide rails toward the outlet station;

a plurality of injection devices configured to inject a sterilization agent into the treatment chamber to apply the sterilization agent to the caps during conveying along one of the first and second guide rails from the inlet station to the outlet station, wherein:
  each one of the injection devices is configured to cooperate with one of the first and second guide rails for injecting the sterilization agent into the treatment chamber and toward one of the first and second guide rails;
a controller configured to actuate the injection devices according to a first and second operative mode;
wherein in the first operative mode, the controller is configured to actuate one of the injection devices cooperating with the first guide rail filled with the caps having the first format during conveying of the caps from the inlet station to the outlet station; and
wherein in the second operative mode, the controller is configured to:
  actuate one of the injection devices cooperating with the first guide rail during conveying of the caps having the first format from the inlet station to the outlet station; and
  actuate another one of the injection devices cooperating with the second guide rail, when the second guide rail is empty during conveying of the caps on the first guide rail.

2. The sterilization apparatus to claim 1, wherein each one of the first and second guide rails is configured to receive, carry, and guide one respective format and/or type of caps or a respective group of format and/or type of caps, and the cap feeder is configured to feed the succession of caps to the respective guide rail being adapted to receive, carry, and guide the format and/or type of caps of the caps.

3. The sterilization apparatus according to claim 1, wherein each injection device includes at least one injection tube arranged adjacent to the respective guide rail and extending at least along an injection portion of the respective guide rail.

4. The sterilization apparatus according to claim 3, wherein the sterilization injection device further includes a sterilization agent distributor, and wherein the controller is configured to control the sterilization agent distributor to selectively supply the sterilization agent to the injection tubes through a respective first end portion and a respective second end portion, and wherein:
  in the first operative mode, the sterilization agent distributor is controlled to supply the sterilization agent to the respective injection tube associated to the first active guide rail through the respective first and second end portions, and
  in the second operative mode, the sterilization agent distributor is controlled to supply the sterilization agent to the respective injection tube associated to the first guide rail through the respective first and second end portions and to the respective injection tube or injection tubes associated to the second guide rail adjacent to the first guide rail through the respective first end portions.

5. The sterilization apparatus according to claim 1, further comprising an expelling device configured to advance the succession of caps along the first guide rail to the outlet station for expelling the caps from the first guide rail.

6. The sterilization apparatus according to claim 5, wherein the expelling device includes a plurality of expelling devices each one associated with one respective guide rail, and wherein each expelling device includes one respective interaction assembly configured to cooperate with the caps received, carried, and guided by the respective guide rail and adapted to move from a relative rest position to the outlet station.

7. The sterilization apparatus according to claim 1, wherein the cap feeder includes an air flow generating device configured to feed the caps to the at least one first guide rail by a flow of air; and
  the sterilization apparatus further comprises a deflector arranged in the area of the inlet station and being configured to restrict the flow of air generated by the air flow generating device within the area of the inlet station.

8. The apparatus according to claim 1, further comprising an air shielding device disposed in the vicinity of the outlet station and configured to hinder entrance of air from an outside space into the treatment chamber through the area of the outlet station.

9. A sterilization apparatus for sterilizing receptacle closures, comprising:
  a treatment chamber having an inlet station and an outlet station;
  a feeding device configured to feed a succession of receptacle closures to the inlet station;
  a conveyor configured to convey the receptacle closures through the treatment chamber from the inlet station to the outlet station;
  an air shielding device disposed in the vicinity of the outlet station and configured to hinder entrance of air from an outside space into the treatment chamber through the area of the outlet station;
  an outlet unit configured to receive the receptacle closures from the conveyor and having a plurality of outlet rails, each outlet rail being configured to receive the receptacle closures from one respective guide rail, and wherein the air shielding device includes a shielding plate arranged within the outlet unit and the outlet rails extend through the shielding plate;
  a sterilization agent injection device configured to inject a sterilization agent into the treatment chamber, wherein:
    the conveyor includes a plurality of adjacent guide rails, each guide rail being configured to receive, carry, and guide a succession of receptacle closures from the inlet station to the outlet station;
    the feeding device is configured to feed the receptacle closures to at least one active guide rail of the plurality of guide rails; and
    the sterilization agent injection device includes a plurality of injection devices, each injection device being associated with one of the guide rails; and
  a controller configured to selectively actuate the injection devices according to a first and second operative mode;
  wherein in the first operative mode, the controller s configured to actuate an injection device associated with the active guide rail; and
  wherein in the second operative mode, the controller is configured to actuate the injection device associated with the active guide rail and an injection device associated with one or more guide rails adjacent to the active guide rail.

10. A method for sterilizing caps, comprising:
  feeding a succession of caps to an inlet station of a treatment chamber;
  conveying the succession of caps through the treatment chamber from the inlet station to an outlet station of the treatment chamber, wherein a conveyor configured to convey the succession of caps through the treatment chamber includes:
a plurality of substantially horizontal guide rails, including:
at least one first guide rail configured to carry and guide caps having a first format; and
at least one second guide rail located adjacent to the first guide rail and configured to carry and guide caps having a second format different from the first format; and
a plurality of pushing devices, each pushing device being selectively activatable for pushing the caps along one of the first and second guide rails toward the outlet station; and
sterilizing the succession of caps while being advanced from the inlet station to the outlet station, wherein:
during the step of sterilizing the caps, a plurality of injection devices are configured to inject a sterilization agent into the treatment chamber to apply the sterilization agent to the caps during the step of conveying along one of the first and second guide rails from the inlet station to the outlet station, wherein each one of the injection devices is configured to cooperate with one of the first and second guide rails for injecting the sterilization agent into the treatment chamber and toward one of the first and second guide rails; and
actuating the injection devices according to a first and second operative modes, wherein:
in the first operative mode, the controller is configured to actuate one of the injection devices cooperating with the first guide rail filled with the caps having the first format during conveying of the caps from the inlet station to the outlet station; and
in the second operative mode, the controller is configured to actuate one of the injection devices cooperating with the first guide rail during conveying of the caps having the first format from the inlet station to the outlet station, and actuate another one of the injection devices cooperating with the second guide rail, when the second guide rail is empty during conveying of the caps on the first guide rail.

11. The method according to claim 10, wherein each one of the first and second guide rails is configured to receive, carry, and guide one respective format and/or type of caps or one respective group of format and/or type of caps, and
during the step of feeding of the succession of caps, the succession of caps is fed to the guide rail being adapted to receive, carry, and guide the format and/or type of caps of the succession of caps.

12. The method according to claim 10, wherein each injection device includes at least one injection tube arranged adjacent to the respective guide rail and extending at least along a portion of the respective guide rail, and wherein during the step of sterilizing the succession of caps, the sterilization agent is selectively supplied to the injection tubes through a respective first end portion and a respective second end portion, and wherein
in the first operative mode, the sterilization agent is supplied to the respective injection tube associated to the first guide rail through the respective first and second end portions; and
in the second operative mode, the sterilization agent is supplied to the respective injection tube associated to the first guide rail through the respective first and second end portions and to the respective injection tube or injection tubes associated to the second guide rail adjacent to the first guide rail through the respective first end portions.

13. The method according to claim 10, wherein the caps are expelled from the active guide rail after interruption of feeding the caps to the active guide rail.

14. The apparatus method according to claim 10, further comprising:
feeding the caps to the at least one first guide rail by a flow of air; and
restricting the flow of air generated by an air flow generating device within the area of the inlet station.

15. A cap sterilization apparatus for sterilizing caps, comprising:
a treatment chamber having an inlet station;
a cap feeder configured to feed a succession of caps to the inlet station;
a conveyor configured to convey the caps through the treatment chamber from the inlet station to an outlet station, the conveyor including:
a plurality of substantially horizontal guide rails, including:
at least one first guide rail configured to carry and guide caps having a first format; and
at least one second guide rail located adjacent to the first guide rail and configured to carry and guide caps having a second format different from the first format; and
a plurality of pushing devices, each pushing device being selectively activatable for pushing the caps along one of the first and second guide rails toward the outlet station;
a plurality of sterilization agent injection devices configured to inject a sterilization agent into the treatment chamber to apply the sterilization agent to the caps during conveying along one of the first and second guide rails from the inlet station to the outlet station, wherein:
each one of the injection devices is configured to cooperate with one of the first and second guide rails for injecting the sterilization agent into the treatment chamber and toward one of the first and second guide rails;
a deflector arranged within the area of the inlet station and configured to restrict the flow of air feeding the receptacle closures to the inlet station within the area of the inlet station: and
a controller configured to actuate the injection devices according to a first and second operative mode;
wherein in the first operative mode, the controller is configured to actuate one of the injection devices cooperating with the first guide rail filled with the caps having the first format during conveying of the caps from the inlet station to the outlet station; and
wherein in the second operative mode, the controller is configured to actuate one of the injection devices cooperating with the first guide rail during conveying of the caps having the first format from the inlet station to the outlet station, and actuate another one of the injection devices cooperating with the second guide rail, when the second guide rail is empty during conveying of the caps on the first guide rail.

16. The apparatus according to claim 15, further comprising an air shielding device configured to hinder entrance of air originating from an outside space through the area of the outlet station into the treatment chamber.

17. The apparatus according to claim 16, further comprising an outlet unit configured to receive the caps from the conveyor and the air shielding device is arranged within the outlet unit.

18. A sterilization apparatus for sterilizing receptacle closures, comprising:
- a treatment chamber having an inlet station and an outlet station;
- a feeding device configured to feed a succession of receptacle closures to the inlet station by a flow of air;
- a conveyor configured to convey the receptacle closures through the treatment chamber from the inlet station to the outlet station;
- a sterilization agent injection device configured to inject a sterilization agent into the treatment chamber; and
- a deflector arranged within the area of the inlet station and configured to restrict the flow of air feeding the receptacle closures to the inlet station within the area of the inlet station,
- wherein the conveyor includes at least one guide rail adapted to receive the receptacle closures and to guide the receptacle closures from the inlet station to the outlet station, and wherein the deflector includes a deflector plate positioned adjacent to the guide rail and configured to swirl the flow of air within the area of inlet station.

19. The apparatus according to claim 18,
- wherein the deflector plate includes a main plate portion parallel to a rectilinear main plate portion of the guide rail and first and second angled plate portions angled with respect to the main plate portion and diverging from opposite side edges of the main plate portion, and
- wherein the first angled plate portion is positioned in the area of the inlet station and is configured to direct the flow of air towards the second angled plate portion, and
- wherein the second angled plate portion is designed to block the propagation of the flow of air in a direction towards the outlet station.

20. The apparatus according to claim 18, wherein the deflector plate is arranged below the guide rail.

* * * * *